(12) United States Patent
Shahidi

(10) Patent No.: US 8,332,007 B2
(45) Date of Patent: Dec. 11, 2012

(54) QUANTITATIVE THREE-DIMENSIONAL MAPPING OF OXYGEN TENSION

(75) Inventor: Mahnaz Shahidi, Northbrook, IL (US)

(73) Assignee: The Board of Trustees of the University of Illinois, Urbana, IL (US)

(*) Notice: Subject to any disclaimer, the term of this patent is extended or adjusted under 35 U.S.C. 154(b) by 523 days.

(21) Appl. No.: 12/686,139

(22) Filed: Jan. 12, 2010

(65) Prior Publication Data

US 2010/0191081 A1 Jul. 29, 2010

Related U.S. Application Data

(60) Provisional application No. 61/143,855, filed on Jan. 12, 2009.

(51) Int. Cl.
*A61B 5/00* (2006.01)

(52) U.S. Cl. .................. 600/323; 600/355; 600/356

(58) Field of Classification Search .............. 600/323, 600/355, 356
See application file for complete search history.

(56) References Cited

U.S. PATENT DOCUMENTS

| | | | |
|---|---|---|---|
| 4,386,098 A | 5/1983 | Woltersdorf, Jr. et al. | |
| 4,416,890 A | 11/1983 | Woltersdorf, Jr. | |
| 4,426,388 A | 1/1984 | Woltersdorf, Jr. | |
| 4,752,115 A * | 6/1988 | Murray et al. ................ | 385/12 |
| 4,797,413 A | 1/1989 | Baldwin et al. | |
| 4,947,850 A * | 8/1990 | Vanderkooi et al. .......... | 600/431 |
| 5,153,192 A | 10/1992 | Dean et al. | |
| 5,240,923 A | 8/1993 | Dean et al. | |
| 5,378,703 A | 1/1995 | Dean et al. | |
| 5,501,225 A * | 3/1996 | Wilson ......................... | 600/478 |
| 5,707,813 A | 1/1998 | Dandliker et al. | |
| 5,837,865 A | 11/1998 | Vinogradov et al. | |
| 6,008,192 A | 12/1999 | Al-Razzak et al. | |
| 6,080,068 A | 6/2000 | Takeda | |
| 6,274,086 B1 * | 8/2001 | Wilson et al. .............. | 422/82.08 |
| 6,348,596 B1 | 2/2002 | Lee et al. | |
| 6,399,392 B1 | 6/2002 | Haugland et al. | |
| 6,701,168 B1 | 3/2004 | Wilson et al. | |

OTHER PUBLICATIONS

Shahidi, M. et al., "Feasibility of Noninvasive Imaging of Chorioretinal Oxygenation", Chorioretinal Oxygenation Imaging, vol. 35(4), pp. 415-422, 2004.

(Continued)

*Primary Examiner* — Clayton E Laballe
*Assistant Examiner* — Warren Fenwick
(74) *Attorney, Agent, or Firm* — Nutter McClennen & Fish LLP

(57) ABSTRACT

Methods and apparatus are disclosed for measuring and mapping oxygen tension in a tissue and, in particular, permit direct non-invasive measurement of retinal tissue oxygen tension. In one aspect, the invention is directed to methods for determining oxygen tension in a target tissue sensitized with an oxygen sensitive probe by imaging the target tissue. In one embodiment, the invention provides a noninvasive method for monitoring oxygen tension in a chorioretinal tissue sensitized with an oxygen sensitive probe. In another aspect, apparatus is disclosed that can determine oxygen tension in tissue by quantifying a signal emitted by an oxygen sensitive probe within the three-dimensional map of a tissue to determine oxygen tension and provide a three-dimensional map of oxygen tension variations.

28 Claims, 7 Drawing Sheets

OTHER PUBLICATIONS

Shahidi, M. et al., "Chorioretinal Vascular Oxygen Tension Canges in Response to Light Flicker", IOVS, vol. 47(11), pp. 4962-4965, 2006.

Shahidi, M. et al., "A Method for Chorioretinal Oxygen: Tension Measurement", Current Eye Research, vol. 31(4), pp. 357-366, 2006.

Shahidi, M. et al., "A Method for Three-Dimensional Imaging of the Retina in Human Eyes", Opthalmic Surgery, Laser & Imaging, vol. 38(1), pp. 35-42, 2007.

Shahidi, M. et al., "Thickness Profiles of Retinal Layers by Optical Coherence Tomography Image Segmentation", AM J Ophthalmol., vol. 146(5), pp. 679-687, 2008.

Shahidi, M. et al., "Three-Dimensional Mapping of Chorioretinal Vascular Oxygen Tension in the Rat", IOVS, vol. 50 (2), pp. 820-824, 2009.

* cited by examiner

QUANTITATIVE THREE-DIMENSIONAL MAPPING OF OXYGEN TENSION

REFERENCE TO RELATED APPLICATION

The present application claims priority to a provisional application entitled "Methods for Quantitative Mapping of Retinal Oxygen Tension" filed on Jan. 12, 2009 and having Ser. No. 61/143,855, which is herein incorporated by reference.

GOVERNMENT SPONSORSHIP

The invention was made with government support under EY017918 awarded by the National Institutes of Health. The government has certain rights in the invention.

TECHNICAL FIELD

The invention relates to methods and apparatus for measuring oxygen tension in tissue and retinal oxygen tension, in particular.

BACKGROUND OF THE INVENTION

Oxygen and nutrients are needed to maintain normal metabolic function of all living tissue. This is especially true for retinal cells. Abnormalities in retinal oxygen delivery and consumption are thought to significantly contribute to the development of retinal diseases. In addition to the role played in acute retinal artery embolic disease, retinal vein occlusion, retinopathy of prematurity and diabetic retinopathy, derangements in retinal oxygenation may also be involved in the development of glaucoma and age-related macular degeneration.

Several techniques have been developed for studying retinal oxygenation based on assessment of choroidal and retinal circulations. Multiwavelength reflectance spectrophotometry measures oxygen saturation of blood in the retinal vasculatures, but the relationship between oxygen tension ($pO_2$) and oxygen saturation of hemoglobin is variable depending on metabolic conditions. Laser Doppler methods have been utilized for measurement of blood flow in retinal and choroidal vasculatures but such methods only provide an indirect measure of vascular $pO_2$.

Retinal tissue oxygenation has also been studied by imaging methods and oxygen-sensitive microelectrodes. Magnetic resonance imaging has been used to study retinal oxygenation response, an indirect measure of retinal tissue $pO_2$, with limited resolution as compared with optical techniques. A fluorescence imaging technique for measurement of retinal $pO_2$ has been reported, but with limited depth resolution. Oxygen-sensitive microelectrodes, measure retinal $pO_2$ directly and with a high depth resolution, but the clinical utility of this technique is limited due to its invasive nature of physically penetrating the tissue. Additionally, microelectrode measurements are typically limited to one-dimensional linear profiles.

There exists a need for improved methods and apparatus for measurement of tissue $pO_2$, especially in the retinal vasculature and tissue. New technologies for assessment of retinal oxygenation are needed to broaden knowledge on disease pathophysiology, and advance diagnostic and therapeutic procedures. In particular, techniques for accurate and precise measurements of oxygen tension would satisfy a long felt need in the field for better diagnostic tools for assessment of retinal function and/or detection of retinal pathologies associated with hypoxia.

SUMMARY OF THE INVENTION

Methods and apparatus are disclosed for measuring and mapping oxygen tension in a tissue and, in particular, for direct non-invasive measurement of retinal tissue oxygen tension ($pO_2$). In one aspect, the invention is directed to methods for determining oxygen tension in a target tissue sensitized with an oxygen sensitive probe by imaging the target tissue. In one embodiment, the invention provides a noninvasive method for monitoring oxygen tension in a chorioretinal tissue sensitized with an oxygen sensitive probe. In another aspect, an apparatus is disclosed that can determine oxygen tension in tissue by quantifying a signal emitted by an oxygen sensitive probe within a three-dimensional map of the tissue to determine oxygen tension and provide a three-dimensional map of oxygen tension variations.

The methods of the present invention can include the steps of: scanning a target tissue sensitized with an oxygen sensitive probe to generate a two-dimensional slice image of a region of the target tissue, obtaining successive two-dimensional slice images through the target tissue, converting the successive two-dimensional images into a three-dimensional map of the target tissue, quantifying the signal from the oxygen sensitive probe within the three-dimensional map of the tissue, wherein the quantification of the oxygen sensitive probe relates to oxygen tension of the target tissue.

In a preferred embodiment, the oxygen sensitive probe can undergo an alteration in the presence of oxygen where the altered probe can be visibly distinct from the non-altered probe. Non-limiting examples of alterations induced by the presence of oxygen can include enzymatic reactions such as quenching of photoluminescence by oxygen, induction of photoluminescence by oxygen, chemical reactions such as oxidation/reduction reactions and others known by those skilled in the art. In a more preferred embodiment, the oxygen sensitive probe can be a phosphorescent probe.

In another aspect of the invention, the method for determining oxygen tension in a target tissue sensitized with an oxygen sensitive probe can include the steps of: obtaining a two-dimensional slice image of a region of the target tissue sensitized with an oxygen sensitive probe; scanning to obtain additional two-dimensional slice images through the target tissue, the slice images being axially offset from each other; converting a series of two-dimensional images into a three-dimensional map of oxygen tension within the target tissue; and quantifying oxygen tension of the target tissue within the three-dimensional map.

The method can further include the step of obtaining a slice image by irradiating the target tissue with radiation that induces photoluminescence of the oxygen sensitive probe and then recording at least one property of the photoluminescence as an image. In one embodiment, the step of irradiating the target tissue can further include irradiating the target tissue with an elongated beam of radiation at an angle such that a slice image is generated in which tissue photoluminescence is axially displaced according to depth position.

The oxygen sensitive probe can be a phosphorescent probe, e.g. a phosphorescent probe emits light of at least one wavelength in a spectrum ranging from about 400 nm to about 900 nm in response to irradiation at an excitation wavelength. And the step of quantifying oxygen tension further comprises quantifying the intensity and/or duration of the secondary light emission from a phosphorescent probe.

The step of obtaining a two-dimensional slice image can further include exciting the oxygen sensitive probe with light to induce secondary light emission; and detecting the secondary light emission from a two-dimensional region of the target tissue to generate a two-dimensional image of the target tissue, wherein the presence of oxygen quenches the light emitted from the probe. The step of exciting the probe can encompass scanning the light projected at an oblique angle in a vertical line across the tissue to excite the probe in a two-dimensional region of the tissue.

The present invention finds particular utility when the target tissue is a chorioretinal tissue. Accordingly, in another aspect of the invention, a noninvasive method for monitoring oxygen tension in a chorioretinal tissue region sensitized with an oxygen sensitive probe can be generally directed to the steps of exciting a region of a chorioretinal tissue sensitized with an oxygen sensitive probe to generate a two-dimensional image of the region, wherein a property of the oxygen sensitive probe is captured in the image; obtaining successive two-dimensional images throughout the region; converting a series of two-dimensional images into a three-dimensional map of the region; and quantifying oxygen tension in the region of the chorioretinal tissue based on the three-dimensional map.

In one embodiment of the invention, the method for monitoring oxygen tension in a chorioretinal tissue region sensitized with an oxygen sensitive probe can comprise obtaining a two-dimensional slice image of a region of the chorioretinal tissue sensitized with an oxygen sensitive probe; scanning to obtain additional two-dimensional slice images through the chorioretinal tissue, the slice images being axially offset from each other; converting a series of two-dimensional images into a three-dimensional map of oxygen tension within the chorioretinal tissue; and quantifying oxygen tension in the region of the chorioretinal tissue within the three-dimensional map. The method can further include a step of comparing the quantified oxygen tension of the region with a known standard.

In yet another aspect of the invention, an apparatus to determine oxygen tension in tissue is disclosed that can include: a light source configured to excite an oxygen sensitive probe present in a region of tissue and generate a responsive emission; a scanner to direct the radiation through a volume of the tissue; a detector to capture responsive emissions; and a processor for quantifying at least one property of the responsive emissions and generating a three-dimensional map of oxygen tension in the volume of the tissue based on variation in at least one property of the captured responsive emissions. In one embodiment, the apparatus can quantify at least the duration or the intensity of responsive emissions.

The apparatus can include a diode laser as a light source. Preferably, a diode laser that generates excitation radiation at a wavelength in a range from about 400 nm to about 900 nm or preferably in a range of about 500 nm to about 600 nm or, more preferably in a range from about 525 nm to about 550 nm.

The apparatus can further include optics for projecting the radiation at an angle relative to a surface of the tissue and an optical chopper to periodically interrupt the radiation. In one preferred embodiment, the optics can include at least one of a spherical lens and a cylindrical lens to shape the excitation radiation into an elongated beam. The scanner can also include a tracking mechanism to compensate for movement of the tissue. Tracking can be particularly useful in measuring oxygen tension of retinal tissue. For example, eye tracker mechanisms currently used in laser vision correction can be readily adapted for use in the present invention.

The apparatus can further comprise a camera to capture a slice image produced by the emission emitted from the oxygen sensitive probe in response to excitation radiation. For example, the camera can be a charge-coupled device (CCD). The apparatus can further comprises a controller to regulate the camera to acquire images at time delayed intervals synchronized with the excitation radiation and thereby acquire a series of slice images offset from each other. In one embodiment, the control function can be performed by a processor that synchronizes the movement of the scanner with the camera image capture to acquire a series of slice images. The processor can also be a computer programmed to generate and store three-dimensional maps of oxygen tension in the volume of tissue.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

DETAILED DESCRIPTION

Figure 1:
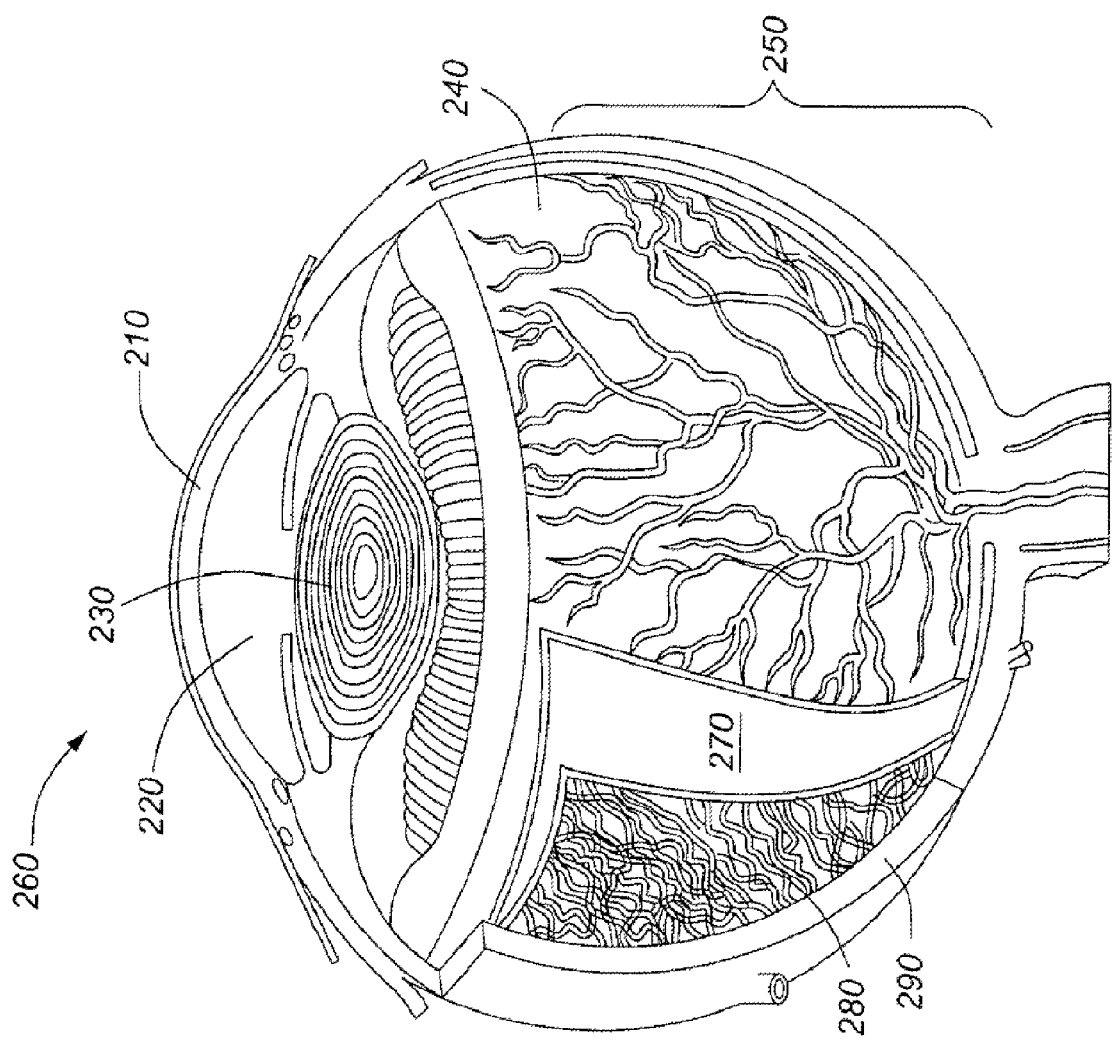
FIG. 1 is a schematic illustration of the tissue layers of the eye.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

All publications, patents and patent applications cited herein, whether supra or infra, are hereby incorporated by reference in their entirety. As used in this specification and the appended claims, the singular forms "a," "an," and "the" include plural references unless the content clearly dictates otherwise. The terms used in this invention adhere to standard definitions generally accepted by those having ordinary skill in the art. In case any further explanation might be needed, some terms have been further elucidated below.

The term "oxygen tension," as used herein, refers to the partial pressure of oxygen in a tissue or fluid. The terms "chorioretinal vasculature," as used herein, refer to the choriodal and retinal vasculature, including the major vessels and capillaries such as the central retinal artery and the choroidal blood vessels. The terms "chorioretinal tissue," as used herein, refer to the choriodal and retinal tissue, including the vasculature. The terms "oxygen sensitive probe," as used herein, refer to a compound that when in the presence of oxygen undergoes an alteration. Non-limiting examples of alterations induced by the presence of oxygen can include enzymatic reactions such as quenching of photoluminescence by oxygen, induction of photoluminescence by oxygen, chemical reactions such as oxidation/reduction reactions and others known by those skilled in the art.

The terms "phosphorescent probe," as used herein, refer to a compound that is photoluminescent when exposed to radiation. Generally, phosphorescent probes absorb radiation within a range of wavelengths (absorption spectra) and emit radiation within a range of lower energy wavelengths (emission spectra).

The terms "light" and "radiation" are used interchangeably and as used herein refer to electromagnetic radiation comprising any wavelength(s). Visible light is radiation that is visible to the human eye. Preferably, the radiation has a wavelength spectrum in the range of about 400 nm to about 900 nm. The radiation can have a wavelength spectrum in a range of about 500 nm to about 800 nm. The radiation can have a wavelength spectrum in a range of about 400 nm to about 700 nm. The radiation can have a wavelength spectrum in a range of about 700 nm to about 900 nm. In some embodiments of the disclosed invention, radiation can comprise wavelengths greater than about 400 nm, 500 nm, 550 nm, 600 nm, 650 nm, 700 nm, 800 nm and 900 nm.

The term "subject" as used herein refers to any living organism in which an immune response is elicited. The term subject includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

In medicine, oxygen tension ($pO_2$) denotes the partial pressure of oxygen, related to the content of oxygen dissolved in a liquid, such as plasma. Each hemoglobin molecule in blood has 4 sites for binding oxygen or $CO_2$. The binding of gas molecules occurs in the presence of a gas mixture as a function to the partial pressure of the gas in the mixture. At low partial pressures of oxygen, most hemoglobin is deoxygenated, meaning some of the oxygen binding sites are not occupied by oxygen and the blood carries less than its optimal amount of oxygen. In an oxygen rich environment (high partial pressure) blood gathers oxygen and each site of the hemoglobin molecule is fully bound to oxygen and it is said to be fully saturated. At around 90% (the value varies according to the clinical context) oxygen saturation increases according to an oxygen-hemoglobin dissociation curve and approaches 100% at partial oxygen pressures of >10 kPa. Oxygen partial pressure is an indicator of oxygen available to those cells consuming oxygen in that region and thus an indication of their metabolic activity and/or the permeability of the blood vessel to allow the oxygen to reach the tissue.

Assessment of oxygenation is important for the diagnosis and understanding of many diseases. Technologies that provide direct measurement of tissue $pO_2$ are needed to supplement knowledge of normal tissue function, as well as, providing a better understanding of development of tissue pathologies associated with hypoxia.

Diabetic retinopathy, the leading cause of blindness in adults, results from abnormal circulation in the retina (National Eye Institute Website). Disease pathology can begin with microaneurysms in the retina as areas of balloon-like swelling in the retina's tiny blood vessels are formed. These blood vessels become blocked depriving portions of the retina of a blood supply. This trauma causes the retina to secrete vascularization signals which result in new, abnormal blood vessels being formed. During this stage, known as proliferative diabetic retinopathy, the abnormal vessels proliferate along the retina and extend to the surface of the vitreous gel that fills the eye. The thin fragile walls of the abnormal vessels eventually leak blood into the vitreous gel causing vision loss and ultimately blindness. In the later phases of the disease, continued abnormal vessel growth and scar tissue may lead to further retinal degeneration including retinal detachment and glaucoma.

Age-related macular degeneration (AMD) affects between ten and fifteen million patients in the United States, and it is the leading cause of blindness in aging populations worldwide. AMD affects central vision and causes the loss of photoreceptor cells in the central part of retina called the macula. Macular degeneration can be classified into two types: dry-form and wet-form. The dry-form is more common than the wet; about 90% of age-related macular degeneration patients are diagnosed with the dry-form. The wet-form of the disease and geographic atrophy, which is the end-stage phenotype of dry-form AMD, causes the most serious vision loss. All patients who develop wet-form AMD are believed to previously have developed dry-form AMD for a prolonged period of time. The exact causes of AMD are still unknown. The dry-form of AMD may result from the senescence and thinning of macular tissues associated with the deposition of pigment in the macular retinal pigment epithelium. In wet-form AMD, new blood vessels grow beneath the retina, form scar tissue, bleed, and leak fluid. The overlying retina can be severely damaged, creating "blind" areas in the central vision.

Decline of vision noticed by the patient or characteristic features detected by an ophthalmologist during a routine eye exam may be the first indicator of AMD. The formation of "drusen," or membranous debris beneath the retinal pigment epithelium of the macula is often the first physical sign that AMD is developing. Late symptoms include the perceived distortion of straight lines and, in advanced cases, a dark, blurry area or area with absent vision appears in the center of vision; and/or there may be color perception changes.

Glaucoma is a broad term used to describe a group of diseases that causes a slowly progressive visual field loss, usually asymptomatically. The lack of symptoms may lead to a delayed diagnosis of glaucoma until the terminal stages of the disease. The prevalence of glaucoma is estimated to be 2.2 million in the United States, with about 120,000 cases of blindness attributable to the condition. The disease is particularly prevalent in Japan, which has four million reported cases. In many parts of the world, treatment is less accessible than in the United States and Japan, thus glaucoma ranks as a leading cause of blindness worldwide. Even if subjects afflicted with glaucoma do not become blind, their vision is often severely impaired.

The progressive loss of peripheral visual field in glaucoma is caused by the death of ganglion cells in the retina. Ganglion cells are a specific type of projection neuron that connects the eye to the brain. Glaucoma is usually accompanied by an increase in intraocular pressure. Current treatment includes use of drugs that lower the intraocular pressure; however, contemporary methods to lower the intraocular pressure are often insufficient to completely stop disease progression.

Ganglion cells are believed to be susceptible to pressure and may suffer permanent degeneration prior to the lowering of intraocular pressure. An increasing number of cases of normal-tension glaucoma are observed in which ganglion cells degenerate without an observed increase in the intraocular pressure.

Importance of oxygen for the human eye is well understood, and retinal hypoxia—a reduction in the delivery of oxygen to the retina—has been implicated as an underlying cause of a number of eye (retinal) diseases such as diabetic retinopathy, diabetic macular edema, age-related macular degeneration, sickle cell disease, retinopathy of prematurity, familial exudative retinopathy, retinal vascular occlusions, ocular ischemic syndrome, and other related conditions. As such diseases progress, there develops some combination of relative impermeability of normally permeable tissues to oxygen diffusion or a closure of retinal capillaries, leading to hypoxia.

The supply of oxygen to the retina is believed to be pertinent to the development of retinal diseases such as macular degeneration and diabetic retinopathy. Under normal healthy conditions, oxygen is delivered to the retina via a dual blood supply, a system called the choroid supplying the outer or deeper layers of the retina, which is not heavily regulated, and a separate inner retinal vascular system that is highly influenced by metabolic feedback from the tissue within the retina, so as to maintain relatively constant oxygen supply.

Retinal oxygen demand under normal conditions is very high (even higher than for the brain) and may be affected by different conditions. The relative contribution of the blood vessels of the inner retinal vasculature and those of the choroid—a layer of vascular tissue behind the retina—to the oxygenation of the retina, in health and disease, is not sufficiently understood. Human retinal oxygen consumption has been difficult to measure because any anesthesia used for in vivo measurements reduces the blood flow to the eye and the invasive nature of the measurement procedure prohibits human data collection.

The eye with its high transparency and surface vasculature offers an opportunity to perform oxygen measurements optically. The measurements are less dependent on tissue variability and can be noninvasive. However, the optics of the eye are complex and this must be taken into account as illustrated by the schematic of the human eye 260 in FIG. 1. The light entering the eye must go through the cornea 210, the aqueous humour 220, the crystalline lens 230 and the vitreous humour 240 before it interacts with the vasculature and tissue of the posterior segment 250 of the human eye 260. Each of these components, cornea 210, the aqueous humour 220, the crystalline lens 230 and the vitreous humour 240, having its own light absorption properties. Furthermore, the eye has two vascular systems, one of which is readily visible in photography and is composed of blood vessels and capillaries within the retina 270, comprising those layers at the back of the eye responsible for vision. The second is a denser vasculature, the choroids 280, that sits behind the retina just before the sclera 290, this being the hard tissue enveloping the whole human eye 260, which supplies oxygen to the deeper layers of the retina 270.

In recent years, chorioretinal imaging modalities, such as indocyanine green angiography, fundus autofluorescence, and optical coherence tomography (OCT), have been developed to permit visualization of retinal tissue and vasculatures. In particular, OCT has become an integral tool for vitreoretinal specialists as it allows high-resolution cross-sectional images of the neurosensory retina to be obtained in a noninvasive manner. However, none of the methods allow for quantitative measurements of oxygen tension within the chorioretinal vasculature or tissue.

The invention is generally directed to a method for determining oxygen tension in a target tissue sensitized with an oxygen sensitive probe comprising obtaining a two-dimensional image slice of a region of the target tissue sensitized with an oxygen sensitive probe, scanning to obtain additional two-dimensional slice images through the target tissue, the slice images being axially offset from each other, converting a series of two-dimensional images into a three-dimensional map of oxygen tension within the target tissue and quantifying oxygen tension of the target tissue within the three-dimensional map.

In a preferred embodiment, the oxygen sensitive probe can undergo an alteration in the presence of oxygen where the altered probe can be visibly distinct from the non-altered probe. Non-limiting examples of alterations induced by the presence of oxygen can include enzymatic reactions such as quenching of photoluminescence by oxygen, induction of photoluminescence by oxygen, chemical reactions such as oxidation/reduction reactions and others known by those skilled in the art. In a more preferred embodiment, the oxygen sensitive probe can be a phosphorescent probe.

It has previously been shown that dissolved oxygen in biological fluids can quench the phosphorescence of certain phosphorescent molecules within the fluids, and that it is possible to measure the oxygen concentration by measuring the quenching of phosphorescence. Oxygen quenching can be used, for example, for a noninvasive, quantitative determination of oxygen tension in the vasculature of tissue in vivo. U.S. Pat. No. 5,837,865 (Vinogradov et al.) discloses phosphorescent molecules that can be used for imaging of the distribution of dissolved oxygen by imaging the phosphorescence of the molecules when exposed to a suitable source of exciting light.

Oxygen quenching reduces both the intensity and the photoluminescence lifetime or decay time of the photoluminescent light, also referred herein as the duration. U.S. Pat. No. 6,701,168 (Wilson et al.) describes a method of measuring the phosphorescence lifetime by the "phase method" in which a phosphorescent sample is repeatedly excited with a periodic pulsed light source. Each pulse of exciting light causes a pulse of phosphorescence, delayed slightly after the exciting pulse. Thus, the periodic exciting pulse train causes a periodic phosphorescent pulse train at the same frequency, but wherein each pulse is delayed. The delay time, which is a measure of the phosphorescence lifetime or duration, is observed as a phase shift between the two pulse trains.

The oxygen sensitive probe can be any luminescent composition disclosed in the above-mentioned U.S. Pat. No. 5,837,865 (Vinogradov et al.), which is incorporated herein by reference in its entirety. Alternatively, the oxygen sensitive probe can be another phosphorescent material suitable for use herein and compatible with the invention described herein. Many such substances are known, and can be referred to as a "probe" or as a "dye," depending on the application. In some embodiments, the probe can have an excitation and emission spectra in the range of about 400 nm to about 900 nm. The probe can have an excitation with a wavelength of about 400 nm, 500 nm, 550 nm, 600 nm, 650 nm, 700 nm and 800 nm. The probe can have an emission with a wavelength of about 400 nm, 500 nm, 550 nm, 600 nm, 650 nm, 700 nm, 800 nm and 900 nm. In one embodiment, the probe can emit light of at least one wavelength in a spectrum ranging from about 400 nm to about 900 nm in response to irradiation at an excitation frequency.

In one embodiment, the oxygen sensitive probe can be a fluorescent or phosphorescent compound. In yet another embodiment, the oxygen sensitive probe can be phosphorescent platinum (II) porphyrin or palladium (II) porphyrin, a fluorescent complex of Ruthenium(II) or Osmium(II), or close analogs or derivatives of these dyes. The probe can be based on a Pt-coproporphyrin or a mono functional reactive derivative thereof conjugated to a macromolecular carrier. The probe can be based on a mono functional reactive derivative of Pt-coproporphyrin which facilitates conjugation to the macromolecular carrier. The probe may be based on Pt(II)-coproporphyrin-ketone, a derivative or close analog thereof. Alternatively, the probe can be based on Pd(II)-coproporphyrin-ketone, a derivative or close analog thereof. The probe can be based on a stable Pt-chlorin or a stable Pd-chlorin. The probe can also be Pd-meso-tetra-(4-carboxyphenyl)porphyrin, glutamate dendrimer of Pd-tetra(4-carboxyphenyl)tetrabenzoporphyrin, glutamate dendrimer of Pd-meso-tetra-(4-carboxyphenyl)porphyrin or a derivative or close analog thereof.

In one embodiment, the oxygen sensitive probe can be a dye covalently linked to the macromolecular carrier. The macromolecular carrier can be a hydrophilic and biocompatible macromolecule. The macromolecular carrier can have a molecular weight in the region of 5,000-200,000 D. In one case, the macromolecular carrier can be a polypeptide, a polynucleotide, a polysaccharide or a synthetic polymer such as poly(acrylate) or poly(ethyleneglycol). The polypeptide can comprise an inert protein such as serum albumin, for example bovine serum albumin (BSA), or an antibody or a fragment thereof.

In another embodiment, the macromolecular carrier can be a cellular targeting polypeptide. In one embodiment, the carrier can be specific to a cellular target, such that the probe has the ability to selectively accumulate in a particular tissue, cell, compartments within the cell, such as mitochondria, lysosomes, inner cell membrane(s), endoplasmic reticulum or at the cell surface. The probe can be intracellular and/or extracellular.

In certain embodiments, the probes can be fluorescent, phosphorescent, photoluminescent or chemiluminescent. The probes can be of fluorescein-family dyes, polyhalofluorescein-family dyes, hexachlorofluorescein-family dyes, coumarin-family dyes, rhodamine-family dyes, cyanine-family dyes, oxazine-family dyes, thiazine-family dyes, squaraine-family dyes, chelated lanthanide-family dyes, BODIPY®-family dyes, and non-fluorescent quencher moieties. Non-fluorescent quencher moieties are substances that reduce, eliminate or control background light emission to enhance detection capabilities. They are typically used in TaqMan probes to reduce or eliminate background emission fluorescence prior to cleavage of the probe oligonucleotide. Other examples of useful materials, probes and substances can be found in U.S. Pat. Nos. 6,399,392, 6,348,596, 6,080,068, and 5,707,813, each of which is hereby incorporated by reference in its entirety.

In one embodiment, a method is generally directed to determining oxygen tension in a target tissue sensitized with an oxygen sensitive probe and the oxygen sensitive probe can be a phosphorescent probe. The phosphorescent probe can undergo an alteration in the presence of radiation or light, such that the phosphorescent probe changes to an excited state and emits an emission spectra or phosphorescence. The method can further comprise irradiating the target tissue with radiation that induces photoluminescence of the oxygen sensitive probe and recording at least one property of the photoluminescence as an image. The properties can comprise quenching of phosphorescence in the presence of oxygen, whereby the quenched phosphorescent probe is no longer visible in the image.

The method can also comprise exciting the oxygen sensitive probe with light to induce a secondary light emission and detecting the secondary light emission from a two-dimensional region of the target tissue to generate a two-dimensional image of the target tissue. The probe can be excited by scanning the light at an oblique angle in a verticle line across the tissue, thereby inducing a secondary light emission from the probe. The presence of oxygen can quench the light emitted from the probe and the duration of the secondary light emission from the phosphorescent probe can be quantified. Quantifying the duration of phosphorescence can comprise quantifying a lifetime of a secondary light emission or an intensity of a secondary light emission from the phosphorescent probe.

The generated two-dimensional image of the tissue comprises an optical section of the tissue. The two-dimensional image can be en face or axial. En face images display the structures of the tissue at a particular depth in the tissue that are parallel to the surface of the tissue. Successive en face images can be compiled to generate a three-dimensional maps through the depth of the tissue. Two-dimensional axial images, perpendicular to the surface of the tissue, display the structures in the tissue at various depths laterally displaced according to their depth location. Successive axial images can be compiled to generate en face images at different tissue depths. In one embodiment, the target tissue can be irradiated with an elongated beam of radiation at an angle such that a slice image is generated in which tissue photoluminescence is axially displaced according to depth position.

The target tissue can be any tissue capable of being imaged. Moreover, the target tissue can be a vascularized tissue, such as vasculature within which blood or other oxygen-carrying liquid circulates. Some non-limiting examples can include the chorioretinal vasculature, the skin, dermal tissue, tongue, or intestine. In one embodiment, the tissue is a chorioretinal tissue.

The invention can also be directed to a noninvasive method for monitoring oxygen tension in a chorioretinal tissue sensitized with an oxygen sensitive probe in a subject. A two-dimensional slice image of the region of chorioretinal tissue can be obtained. The region of chorioretinal tissue can be scanned multiple times to obtain additional two-dimensional slice images through the chorioretinal tissue and the slice images being axially offset from each other. A series of two-dimensional images can be converted into a three-dimensional map of oxygen tension within the chorioretinal tissue. Then the oxygen tension can be quantified in the region of the chorioretinal tissue within the three-dimensional map.

In another aspect of the invention, spectral data can be collected from a continuous range of wavelengths from about 400 nm to about 900 nm, including spectra from transmitted or reflected light or radiation. With this method, noninvasive, in vivo measurements of relative oxygen tension can be obtained using emission spectra from an oxygen sensitive probe. This method could also measure oxygen tension from blood vessels other than the chorioretinal vasculature, e.g., skin, tongue, or intestine. This method was used to generate three-dimensional maps of chorioretnal vasculatures indicating relative oxygen tension. Changes in oxygen tension can be monitored with the disclosed method for early detection of disease, e.g., diabetic retinopathy or glaucoma. This method can also be used to monitor oxygen treatments for eye diseases, wounds or burns.

As will be appreciated by the skilled artisan, the route and/or mode of administration will vary depending upon the tissue to be imaged. The probe can be administered intravenously or intravitreally. The probe can also be administered orally, for example, with an inert diluent or an assimilable edible carrier. The probe (and other ingredients, if desired) can also be enclosed in a hard or soft shell gelatin capsule, compressed into tablets, or incorporated directly into the subject's diet. For oral administration, the probe can be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

The probe can be administered in a liquid form. The pharmacological agent should be soluble in a variety of solvents, such as for example, methanol, ethanol, and isopropanol. A variety of methods are known in the art to improve the solubility of the pharmacological agent in water and other aqueous solutions. For example, U.S. Pat. No. 6,008,192 to Al-Razzak et al. teaches a hydrophilic binary system comprising a hydrophilic phase and a surfactant, or mixture of surfactants, for improving the administration of compounds.

Other methods for improving the delivery and administration of the probe can include means for improving the ability of the probe to cross membranes, and in particular, to cross the blood-brain barrier. In one embodiment, the probe can be modified to improve its ability to cross the blood-brain barrier, and in an alternative embodiment, the probe can be co-administered with an additional agent, such as for example, an anti-fungal compound, that improves the ability of the probe to cross the blood-brain barrier.

In one aspect of the invention, the subject can have a condition selected from the group consisting of diabetes, macular degeneration, retinopathy and glaucoma. Monitoring oxygen tension can be indicative of a predisposition to one of the conditions or likelihood of developing one of the conditions for the subject. Monitoring can also comprise scanning multiple regions of the chorioretinal tissue. By scanning multiple regions, oxygen tension can be evaluated in different areas of the tissue, variable distances from the vasculature as well as determining differences between diseased and healthy tissue areas.

Moreover, repeated measurements can be done to monitor oxygen tension over a time interval. The time interval can comprise 6 hours, 12 hours, 24 hours, 3 days, 4 day, 5 day, 1 week, 2 weeks, 3 weeks, 1 month, 2 months, 3 months, 4 months, 6 months, 9 months, 1 year, 2 years, 3 years, 4 years, 5 years and longer. Furthermore, the subject can be treated to improve oxygenation in a region of the chorioretinal tissue if the oxygen tension is below a known standard. By comparing the quantified oxygen tension of the tissue to a known standard, wherein the known standard can be oxygen tension of healthy tissue, oxygen tension of healthy tissue surrounding the target tissue, oxygen tension of previous measurements, or other values known by one skilled in the art, assessments can be made to treat the subject to improve oxygenation of the target tissue.

In one embodiment, a method for increasing oxygen tension in chorioretinal tissues in a patient by methods known in the art. One such method can be administering a carbonic anhydrase inhibitor (CAI) either orally, intraveneously or topically such as those which are described in U.S. Pat. Nos. 4,797,413, 4,386,098, 4,416,890, 4,426,388, 5,378,703, 5,240,923 and 5,153,192; and the like. A preferred method is the administration of a topical carbonic anhydrase inhibitor.

Another embodiment can utilize a hypotonic solution of xanthan gum and a carbonic anhydrase inhibitor, preferably a hypotonic solution of xanthan gum and a topical carbonic anhydrase inhibitor to increase oxygen tension in chorioretinal tissues.

Another method for increasing oxygenation in tissues is the use of molecules capable of transporting, delivering and/or supplying oxygen to cells, thus supporting viability, proliferation, differentiation and/or migration of cells. Some non-limiting examples can be hemoglobin-based molecules or a perfluorocarbon molecule or a derivative thereof.

In another embodiment, a method for increasing oxygen tension is by enhancing, structuring and/or prestructuring oxygen includes, introducing oxygen into a vessel through an inlet of the vessel, directing the oxygen through a magnetic flux, outputting the oxygen through an outlet of the vessel. Laser treatment can also allow oxygen that normally diffuses from the choriocapillaris into the retina to diffuse through laser scars in the photoreceptor layer without being consumed in the mitochondria of the photoreceptors. Additionally, treatment with antibodies to growth factors such as vascular endothelial growth factor (VEGF) can reduce pathological neovascularization.

Another aspect of the invention is directed to an apparatus for determining oxygen tension in tissue. The apparatus can comprise a light source configured to project radiation to excite an oxygen sensitive probe present in a region of tissue and generate a responsive emission, a scanner to direct the radiation through a volume of the tissue, a detector to capture responsive emissions and a processor for quantifying at least one property of the responsive emissions and generating a three-dimensional map of oxygen tension in the volume of the tissue based on variation in the at least one property of the captured responsive emissions. Furthermore, in one embodiment, the apparatus can be configured to quantify at least the duration of responsive emissions. In another embodiment, the apparatus can be configured to quantify at least the intensity of responsive emissions.

Figure 2:
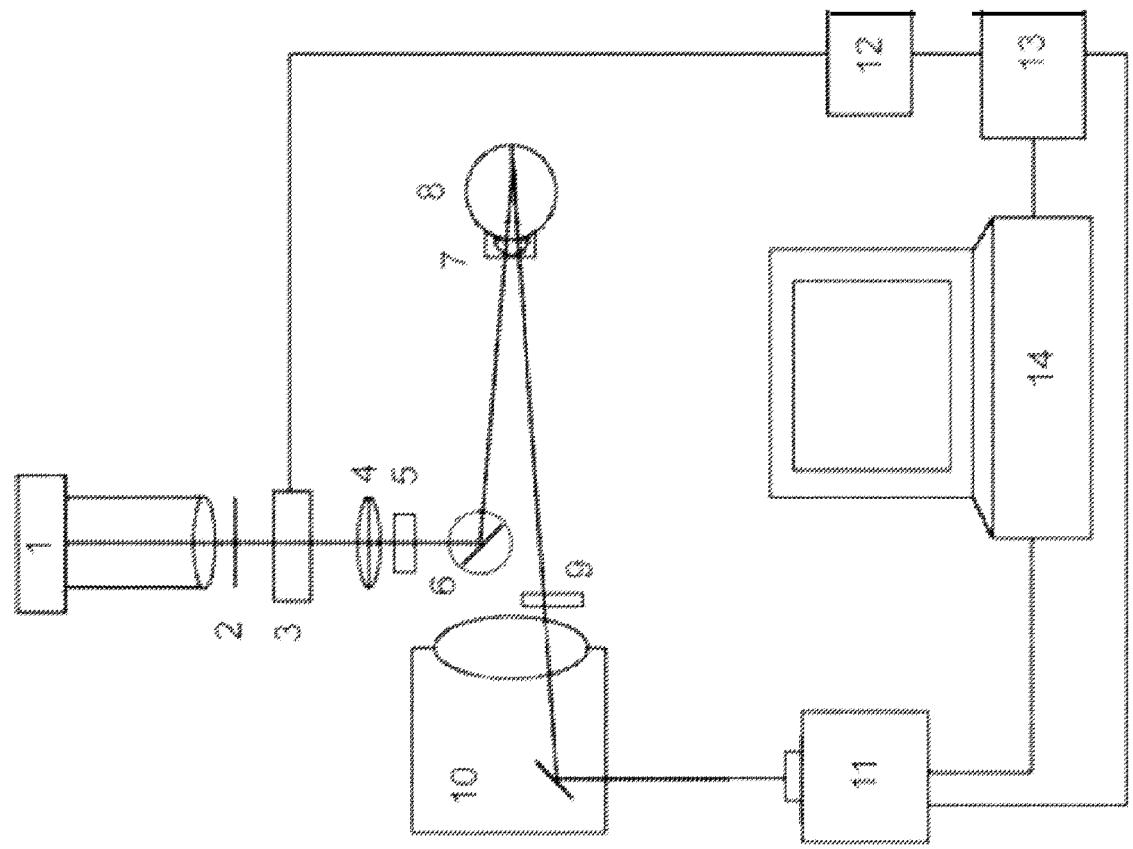
FIG. 2 is a block diagram showing one embodiment of an apparatus according to the invention.

In FIG. 2 an apparatus according to the invention is shown including a laser, 1, which is connected to a filter, 2, and an optical chopper, 3, which is controlled by a chopper controller, 12. Two lens, a spherical lens, 4, and a cylindrical lens, 5, focus the laser beam from the laser, 1. A galvanometer scanner, 6, controls the movement of the laser over a section of the eye, 8, which is covered by an optional contact lens, 7. An infrared filter, 9, filters light emitted from the eye, 8, and converted to an image in a slitlamp biomicroscope, 10, and captured in an intensified camera, 11, controlled by a camera controller, 13. The images are processed by a computer, 14, to calculate the oxygen tension in the section of eye.

The radiation from the light source can excite the oxygen sensitive probe within the tissue, thereby producing an emission that can be quantified. The light source can be a separate light source or it can be integrated as a component of another element of the apparatus. The light source can be integrated as a component of a biomicroscope, binocular indirect opthalmoscope or an analogous instrument known by one skilled in the art. In one embodiment, the light source can be delivered through a magnifying system designed to examine living tissue. In one embodiment, the light source can be delivered through a slit lamp biomicroscope to examine ocular tissues. Furthermore, the light source can be a diode laser.

The light source can also generate radiation with wavelengths of greater than about 400 nm, 500 nm, 550 nm, 600 nm, 650 nm, 700 nm, 800 nm and 900 nm. In one embodiment, the light source can generate excitation radiation with wavelengths in a range of about 400 nm to about 900 nm. The excitation radiation can have a wavelength spectrum in a range of about 500 nm to about 800 nm. The excitation radiation can have a wavelength spectrum in a range of about 400 nm to about 700 nm. The excitation radiation can have a wavelength spectrum in a range of about 700 nm to about 900 nm. In another embodiment, the light source can generate excitation radiation with wavelengths in a range of about 500 nm to about 600 nm. In yet another embodiment, the light source can generate excitation radiation with wavelengths in a range of about 525 nm to about 550 nm. In a further embodiment, the light source can generate excitation radiation at a wavelength in the visible spectrum.

In another embodiment of the invention, a responsive emission can be emitted from the oxygen sensitive probe in response to excitation radiation. The responsive emission can be, but is not limited to, emission of light, phosphorescence, photoluminescence, chemical alterations and enzymatic reactions. In a preferred embodiment, the responsive emission is light or radiation. The responsive emission can have a wavelength greater than about 400 nm, 500 nm, 550 nm, 600 nm, 650 nm, 700 nm, 800 nm and 900 nm. In one embodiment, the responsive emission has a wavelength that is sufficiently different than the excitation wavelength and can be separated with a filter. In another embodiment, the responsive emission can have a wavelength in a range of about 400 nm to about 900 nm. The responsive emission can have a wavelength spectrum in a range of about 500 nm to about 800 nm. The responsive emission can have a wavelength spectrum in a range of about 400 nm to about 700 nm. The responsive emission can have a wavelength spectrum in a range of about 700 nm to about 900 nm. The responsive emission can have a wavelength in a range of about 600 nm to about 700 nm. The responsive emission can have a wavelength in a range of about 625 nm to about 670 nm.

In one embodiment the apparatus can further comprise a filter. The filter can filter radiation of specific wavelengths or a range of specific wavelengths. In a preferred embodiment, the filter allows radiation of wavelengths in a visible spectrum to pass through. In another embodiment, the filter allows radiation of wavelengths in a range of about 400 nm to about 900 nm to pass through. The filter can allow radiation of wavelengths of about 500 nm to about 600 nm to pass through. The filter can allow radiation of wavelengths of about 525 nm to about 550 nm to pass through. The filter can allow radiation of wavelengths of about 625 nm to about 670 nm to pass through. In yet another embodiment, the filter can be an infrared filter.

In another embodiment of the invention, the apparatus can comprise optics to project the radiation on the tissue. The optics can comprise at least one lens to shape the excitation radiation into an elongated beam. The lens can be at least one of a spherical lens and a cylindrical lens. Furthermore, the lens can project the radiation or light at an angle relative to a surface of the tissue. The angle can be an oblique angle such that the radiation is projected in a vertical line across the tissue. An oblique angle can cause the radiation or light to intersect the target tissue at the same angle to produce a two-dimensional view of the tissue. The angle can be in the range of about 1% to 20% between the incident light source and the imaging path. The angle can be greater than about 1%, 2%, 3%, 4%, 5%, 6%, 7%, 8%, 9%, 10%, 11%, 12%, 13%, 14%, 15%, 16%, 17%, 18%, 19% and 20%. In a preferred embodiment, the oblique angle is about 10%.

In yet another embodiment of the invention, the apparatus can comprise an optical chopper. The optical chopper can disrupt the radiation emitted from the light source to periodically interrupt the radiation and/or light from the light source. A separate control device can also be used to control the frequency and duration of the radiation disruption by the optical chopper. The optical chopper can be set at a frequency of about 1000 Hz, 1100 Hz, 1200 Hz, 1300 Hz, 1400 Hz, 1500 Hz, 1600 Hz, 1700 Hz, 1800 Hz, 1900 Hz and 2000 Hz. In a preferred embodiment, the optical chopper can be set at a frequency of about 1600 Hz. Phase shifts can be set for about 0° and about 180° of the frequency. Phase shifts can also be set for any of 0°, 30°, 45°, 60°, 90°, 120°, 135°, 150° and 180° of the frequency.

The apparatus can also comprise a scanner. The scanner can deflect the radiation to move across a section of the tissue. Some non-limiting examples of scanners for use with the apparatus can be a galvanoscanner, a resonant mirror scanner, an acoustic optical modulator, a polygonal scanner and/or a microelectromechanical scanner. The scanner can be driven to rotate in an arc, in an oscillating motion or in a manner appropriate for irradiating a desired section of tissue. In another embodiment, the scanner can comprise a tracking mechanism. The tracking mechanism can align (move) the irradiation position even if the tissue moves during irradiation.

The apparatus can further comprise a detector to capture responsive emissions. The detector can be a biomicroscope, binocular indirect opthalmoscope or an analogous instrument known by one skilled in the art. The biomicroscope can be designed for detailed examination of ocular tissues containing a magnifying system.

In one embodiment, the detector can be a camera to capture responsive emissions from the light emitted from the oxygen sensitive probe to produce an image. The camera can be a charge-coupled device. The camera can also be an intensified camera. Other examples of cameras can be used to capture the images as one skilled in the art would be familiar with. Moreover, the camera can be synchronized with the scanner to obtain two-dimensional images of the tissue that is scanned. The camera can also capture images of the light emitted from the oxygen sensitive probe to produce a two-dimensional image of the tissue. Additionally, the camera can be controlled by a separate camera control device or another element of the apparatus. The camera control device can regulate the camera to acquire images at time delayed intervals synchronized with movement of the scanner thereby acquiring a series of slice images offset from each other.

The apparatus can also comprise a processor. The processor can quantify the duration of the responsive emission emitted from the oxygen sensitive probe or an intensity of the responsive emission to determine oxygen tension in the section of the tissue. The processor can control the tissue scanning by synchronizing the scanner and detector to capture a series of slice images. Additionally, the processor can have an input/output control, memory, electronic circuitry made of digital circuitry, analog circuitry, or both and can be programmable. In a preferred embodiment, the processor can be a computer. The computer can have a software program to synchronize the scan rate with the acquisition of the responsive emission emitted from the oxygen sensitive probe to quantify the duration of emitted light. Additionally, the processor can synchronize the scan rate of the scanner with the camera to obtain two-dimensional slice images, as well as a series of slice images. The processor can also act as a controller for the camera, optical chopper or any other element of the apparatus.

The processor can be a computer programmed to convert the quantification of the emission, e.g. light, radiation, phosphorescence, emitted from the oxygen sensitive probe into oxygen tension values for a two-dimensional slice of the tissue or a three-dimensional section of the tissue. Moreover, the computer can have a software program to convert the successive two-dimensional images obtained from the scanner and camera into a three-dimensional section of the tissue. In one embodiment, the process can be programmed to acquire and store three-dimensional maps of oxygen tension in the volume of tissue.

Figure 3:
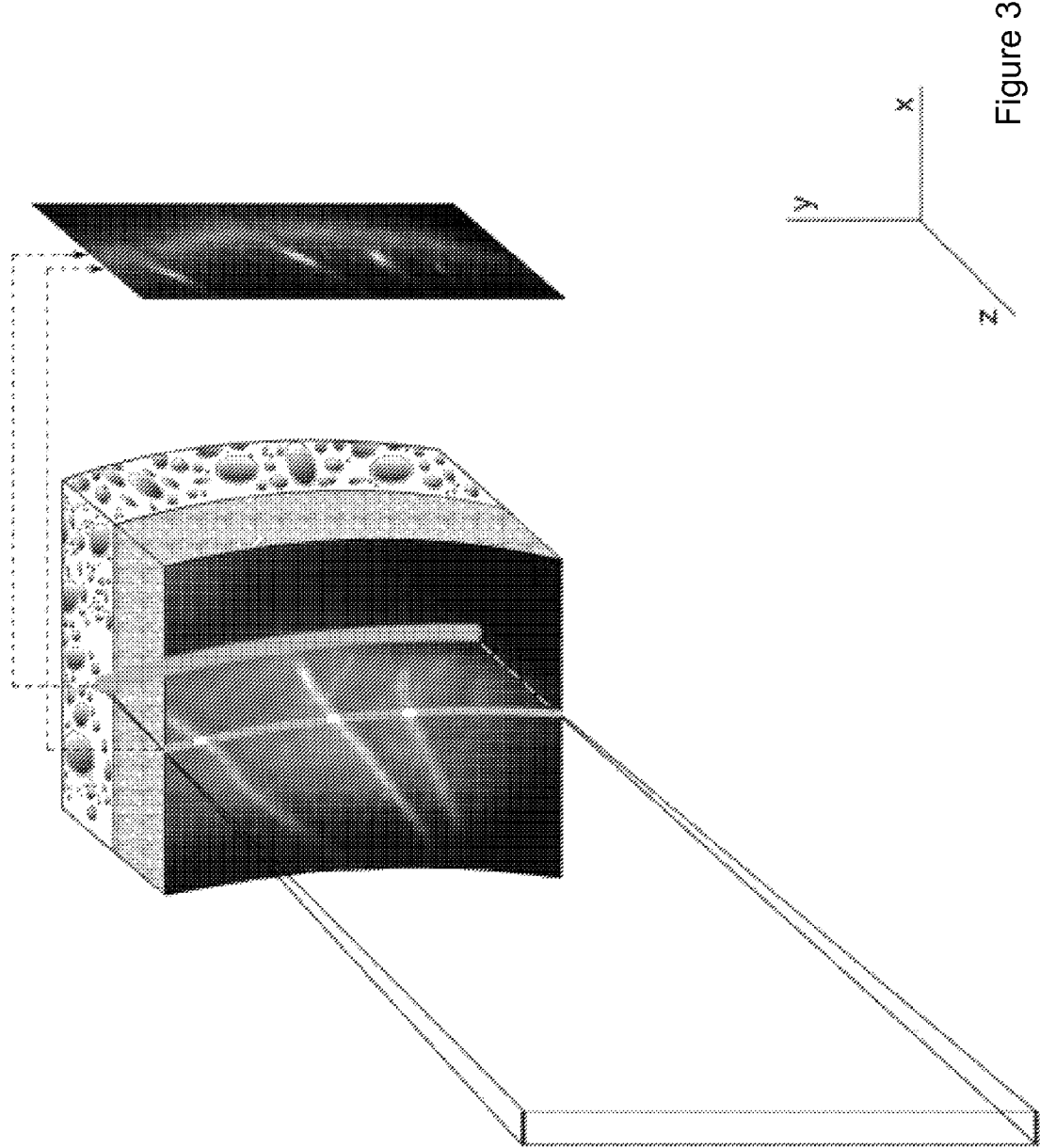
FIG. 3 is a schematic illustration of a method according to the invention for capturing a slice image.

FIG. 3 further illustrates the methods and apparatus of the invention. As illustrated an elongated laser beam is projected at an angle onto a retina after intravenous injection of an oxygen sensitive molecular probe to generate an optical section phosphorescent image in the Y-Z plane of the retina. Since the incident beam is not coaxial with the viewing axis, chorioretinal vasculatures appear laterally displaced according to their depth position in the slice image captured by the detector.

Figure 4:
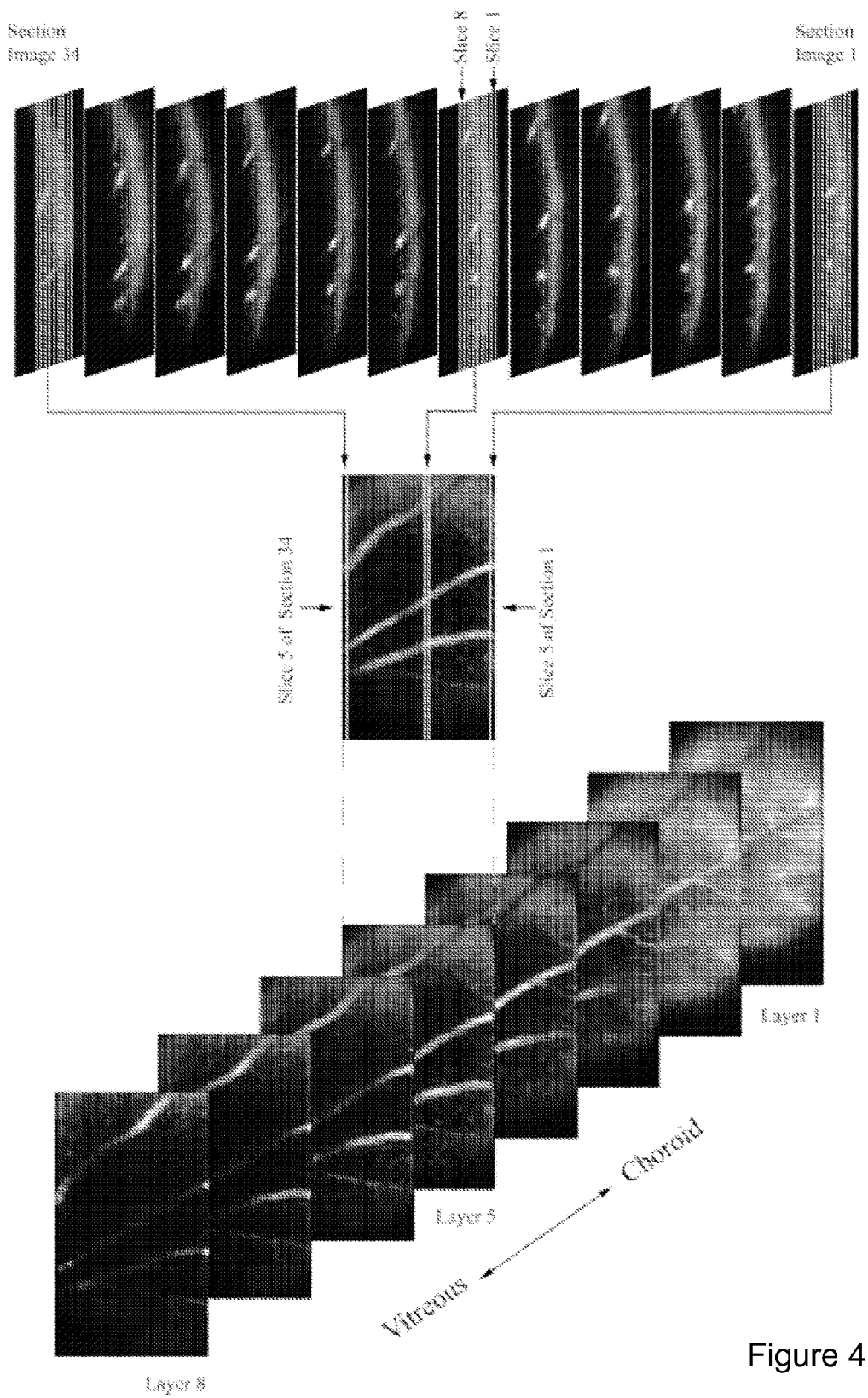
FIG. 4 is a schematic illustration of a method according to the invention for processing a plurality of slice images.

FIG. 4 illustrates one preferred mapping technique. The 2D optical section phosphorescence images (as shown in FIG. 3) in the Y-Z retinal plane can be processed to generate 3D phosphorescence retinal images at different retinal depths. Every third optical section phosphorescence image from a series of 34 images can be acquired during a laser scan, as displayed in FIG. 4 (top). Each 2D optical section phosphorescence image can be segmented into vertical slices in depth by an automated software algorithm developed in Matlab (The Mathworks Inc., Natick, Mass.). The slices can be separated in depth by 20 microns and encompassed the retinal thickness. The first slices from each 2D optical section phosphorescence images in the series can be placed next to each other to construct an en face phosphorescence intensity image of the first retinal vascular layer. An example of the reconstructed en face phosphorescence intensity image of layer 5, generated by combining the fifth slice from each image, is shown in FIG. 4 (middle).

This process can be repeated to generate a set of en face phosphorescence intensity images of retinal layers, separated by 20 microns in depth (FIG. 4, bottom). For each depth-displaced layer, a set of phase-delayed phosphorescence intensity images can be constructed using the same reconstruction technique.

The methodology for quantitative measurement of $pO_2$ based on 2D phase-delayed phosphorescence intensity images has been previously described. A frequency-domain approach can be used for measuring phosphorescence lifetime by varying the phase delay between the modulated excitation laser and the sensitivity of the phosphorescence imaging camera. The $pO_2$ can be determined from the lifetime according to the Stern-Volmer expression: $pO_2=(\tau_0/\tau-1)/(\kappa Q)(\tau_0)$, where $\tau$ is the phosphorescence lifetime and $\kappa Q$ and $\tau_0$ are the probe's quenching constant and lifetime in a zero oxygen environment, respectively. $pO_2$ was calculated at each pixel on the image with previously published $\kappa Q$ and $\tau_0$ values of 381 mm $Hg^{-1}*s^{-1}$ and 637 microseconds, respectively. As in FIG. 4, three-dimensional $pO_2$ maps can be generated by mapping $pO_2$ in each of the eight depth-displaced retinal layers.

To determine $pO_2$ in the choroid, retinal arteries, and veins, $pO_2$ images can be processed. A mask can be generated by global thresholding of the phosphorescence intensity image (at zero phase delay) for each layer. The mask can be assigned a value of 0 or 1 to image pixels based on intensity levels. Then the mask can be multiplied by the $pO_2$ map for each corresponding layer. Regions of interest can be selected on a layer closest to the choroid and a layer on which a retinal artery and vein can be visible. Average $pO_2$ measurement in the choroid, retinal arteries, and veins can be calculated. For determining $pO_2$ in the retinal capillaries, a mask can be generated by local thresholding of the phosphorescence intensity image (at zero phase delay) for a layer on which capillaries are best visualized and in a region between a retinal artery and a vein. The mask can be multiplied by the $pO_2$ map for the corresponding layer, and average $pO_2$ in the capillaries can be calculated. To eliminate the contribution of noise caused by light scatter, only best-fitted phaseangle calculations ($R^2>0.9$) and $pO_2$ measurements within normal physiological conditions (<100 mm Hg) can be included for calculation of averaged chorioretinal vascular $pO_2$ measurements.

EXAMPLES

Materials and Methods

The instrument for optical section phosphorescence imaging is shown in FIG. 2 and discussed above. The slit lamp biomicroscope was modified to project a narrow focused laser line at an angle on the retina and image the reflected/scattered light from the retina. Due to the 10-degree angle between the incident laser and imaging path, an optical section retinal image was acquired by a digital camera. For phosphorescence imaging, the laser wavelength matched with the excitation wavelength of the molecular probe and a filter with transmission overlapping the phosphorescence emission was placed in the imaging path.

The phosphorescence lifetime of an oxygen-sensitive molecular probe was measured using a frequency-domain approach as previously described. The laser light and sensitivity of the camera were independently modulated at a frequency of 1600 Hz. The phase between the 2 modulators was incrementally delayed and a set of 10 optical section phosphorescence images were acquired at 74 μs intervals, thereby producing phase shifts between 0° and 180°. The phase-delayed images were analyzed to determine phosphorescence lifetime which is related to the $pO_2$ according to the Stern-Volmer expression: $\tau_0/\tau=1+(\kappa_Q)(\tau_0)(pO_2)$, where $pO_2$ (mm Hg) is the oxygen tension, $\tau$ (μsec) is the phosphorescence lifetime, $\kappa_Q$ (1/mm Hg μsec) is the quenching constant for the triplet-state phosphorescence probe, and $\tau_0$ is the lifetime in zero oxygen environment. At each pixel on the image, retinal $pO_2$ was calculated and depicted by pseudo-color mapping. An oxygen profile through the retinal depth was derived by plotting averaged $pO_2$ values over 200-micron vertical segments on the retinal $pO_2$ map. A mean oxygen profile was computed by averaging 14 profiles from consecutive vertical segments. Maximum, minimum, and slope of outer retina $pO_2$ profile, and mean of inner retina $pO_2$ were calculated. The systemic arterial $pO_2$, maximum outer retina $pO_2$, and difference between maximum and minimum outer retina $pO_2$ measurements obtained during $FiO_2=10\%$, 21%, and 50% were statistically compared using analysis of variance (ANOVA). Linear regression analysis was performed to determine the correlation between maximum outer retina $pO_2$ and systemic arterial $pO_2$, slope of the outer retina $pO_2$ profile, or mean inner retina $pO_2$. Statistical significance was accepted at $P<0.05$.

Animals

Ten male Long Evans pigmented rats (450-650 g) were used for the study. The animals were treated in compliance with the ARVO Statement for the Use of Animals in Ophthalmic and Vision Research. The rats were anesthetized using Ketamine (85 mg/kg IP) and Xylazine (3.5 mg/kg IP). The pupils were dilated with 2.5% phenylephrine and 1% tropicamide. The oxygen-sensitive molecular probe, Oxyphor R2 (Oxygen Enterprises, Ltd. Philadelphia, Pa.) was dissolved in saline and 3 µl (0.5 mM) was injected intravitreally. The presence of probe in the vitreous was confirmed immediately following injection by imaging to visualize a bolus in the vitreous cavity. Animals were imaged 24 hours post injection, which was the optimum time needed for the probe to diffuse from the vitreous into the retina. Prior to imaging, 1% hydroxypropyl methylcellulose was applied to the cornea and a glass cover slip was placed on the cornea in order to eliminate its refractive power and to prevent corneal dehydration. Body temperature was maintained between 37° C. and 38° C. via a copper tubing water heater. The rat was placed in front of the imaging instrument. The laser power was adjusted to 100 µW, which is safe for viewing according to the American National Standard Institute for Safety Standards.

The fraction of inspired oxygen was varied in via a high-flow face mask system. Gas mixtures containing 10%, 21% (room air), and 50% were administered to the rats 10 minutes before and during retinal $pO_2$ imaging. During administration of the 3 $FiO_2$, arterial blood was drawn through a femoral artery catheter and sent for blood gas analysis to provide measurements of systemic arterial $pO_2$. During $FiO_2$=10%, 21%, and 50%, imaging was performed in 6, 6, and 4 rats, respectively. Under each $FiO_2$ condition, 3 sets of phase-delayed optical section phosphorescence images were acquired.

Results

Figure 5:
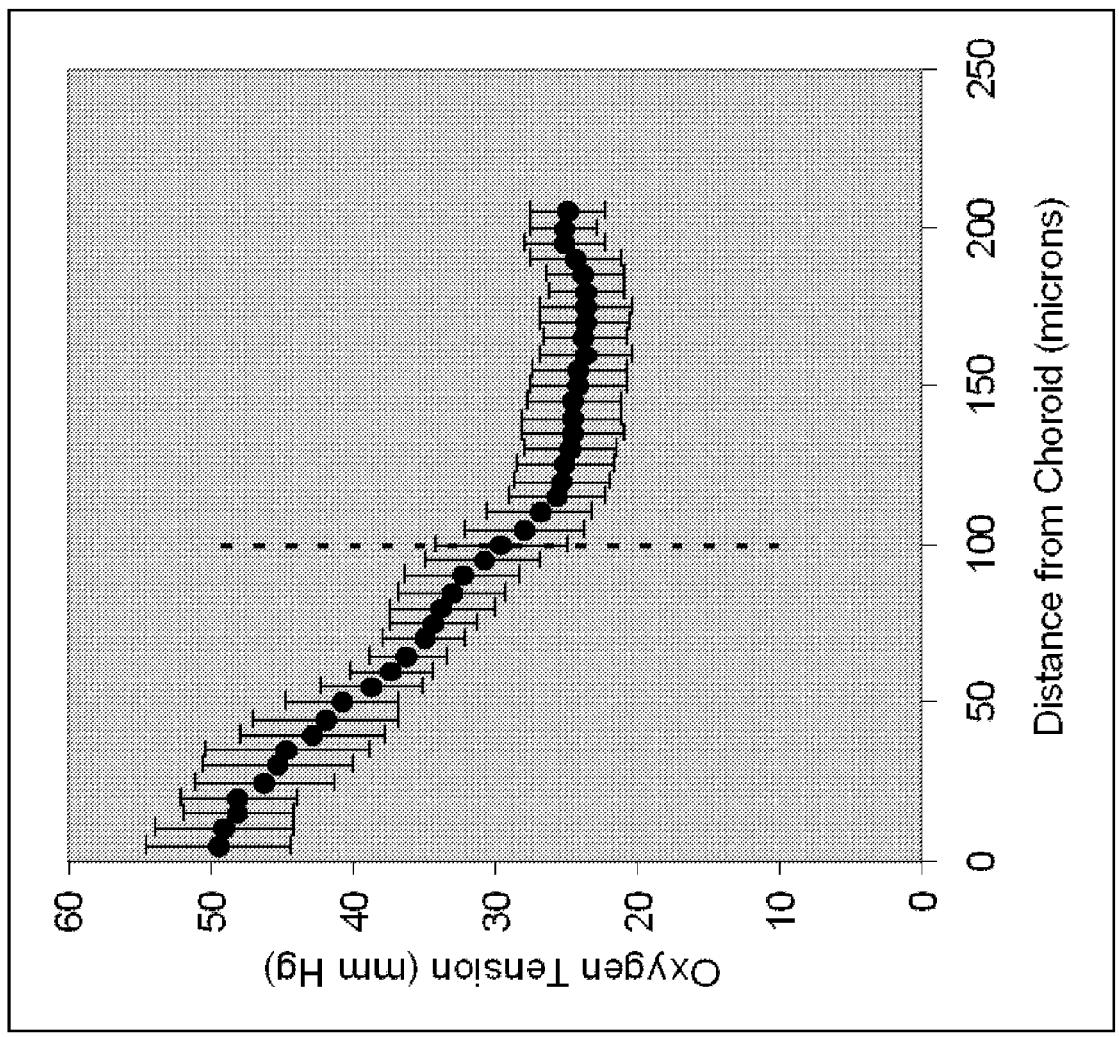
FIG. 5 depicts an example of a retinal $pO_2$ profile derived from a retinal $pO_2$ map.

An optical section phosphorescence image, displaying a cross sectional view of the retina during $FiO_2$=21% was generated in a rat. The phosphorescence from the probe is visualized distinctly in the retinal tissue. The phase-delayed optical section phosphorescence images were analyzed and a retinal $pO_2$ map was generated in the Y-Z plane of the retina. Retinal $pO_2$ was highest at the choroidal interface and decreased incrementally through the retinal depth. A mean oxygen profile was derived from the retinal $pO_2$ map (FIG. 5). The maximum and minimum of outer retinal $pO_2$ measurements were 49 and 28 mm Hg, respectively. The slope of the outer retina $pO_2$ profile was −0.22 mm Hg/micron. The mean of the inner retina $pO_2$ was 25 mm Hg.

The systemic arterial $pO_2$ was found to vary according to the $FiO_2$. Under $FiO_2$=10%, 21% and 50%, the mean systemic arterial $pO_2$ in was measured to be 41±11 mm Hg, 54±8 mm Hg, and 152±31 mm Hg, respectively. Systemic arterial $pO_2$ measurements obtained during the 3 oxygen breathing conditions were significantly different (P<0.001). The maximum outer retina $pO_2$ measurements obtained during $FiO_2$=10%, 21%, and 50% were 38±15, 54±13, and 76±21 mm Hg, respectively (P=0.009). The maximum outer retina $pO_2$ was highly correlated with systemic arterial $pO_2$ (r=0.6; P=0.01; N=16). The intrasubject variabilities of maximum outer retina $pO_2$ determined from standard deviations of repeated measurements in the same eye were 4, 6, and 6 mm Hg, during $FiO_2$=10%, 21%, and 50%, respectively.

Figure 6:
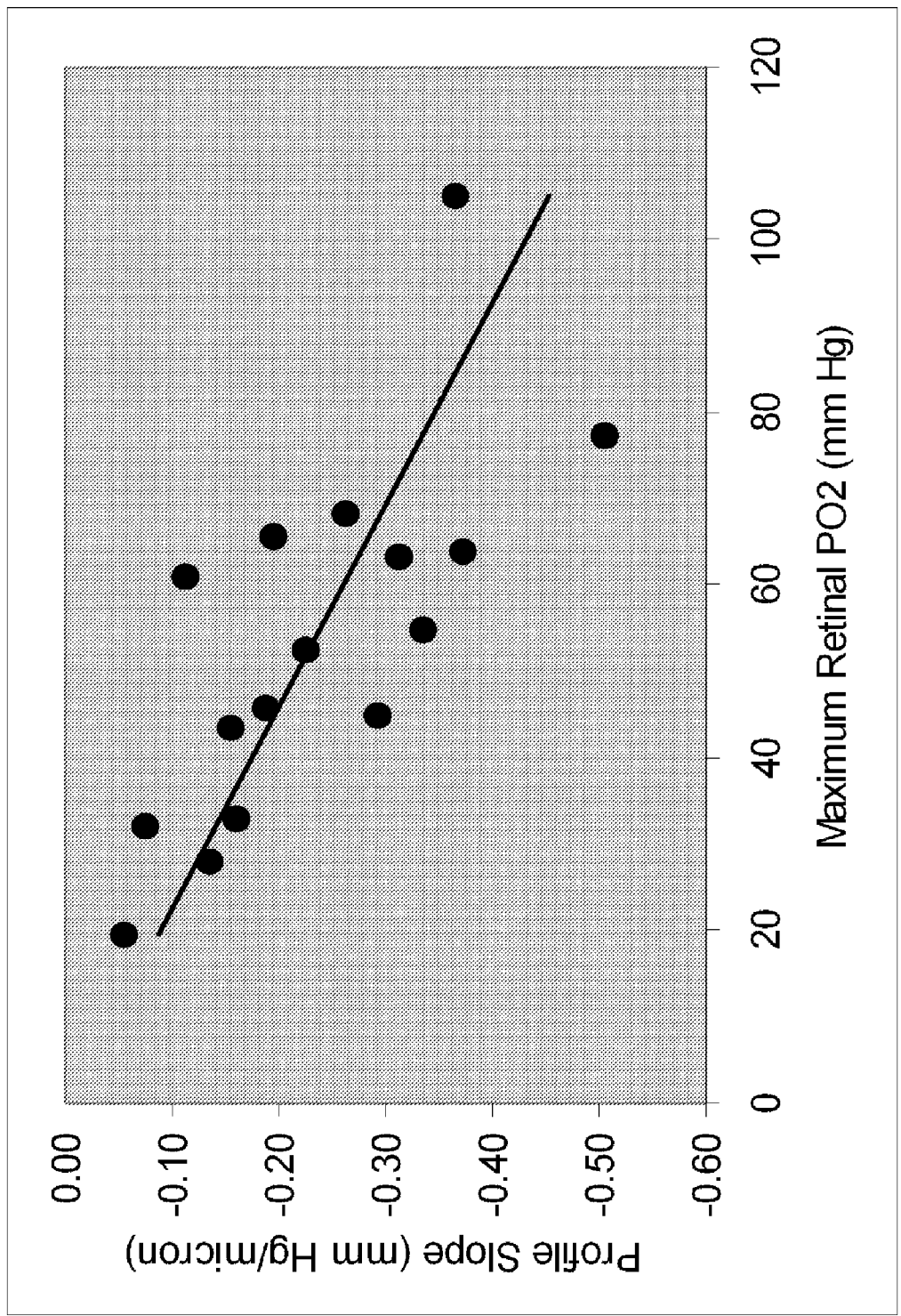
FIG. 6 illustrates the relationship between slope of the outer retina $pO_2$ profile and maximum outer retina $pO_2$.
Figure 7:
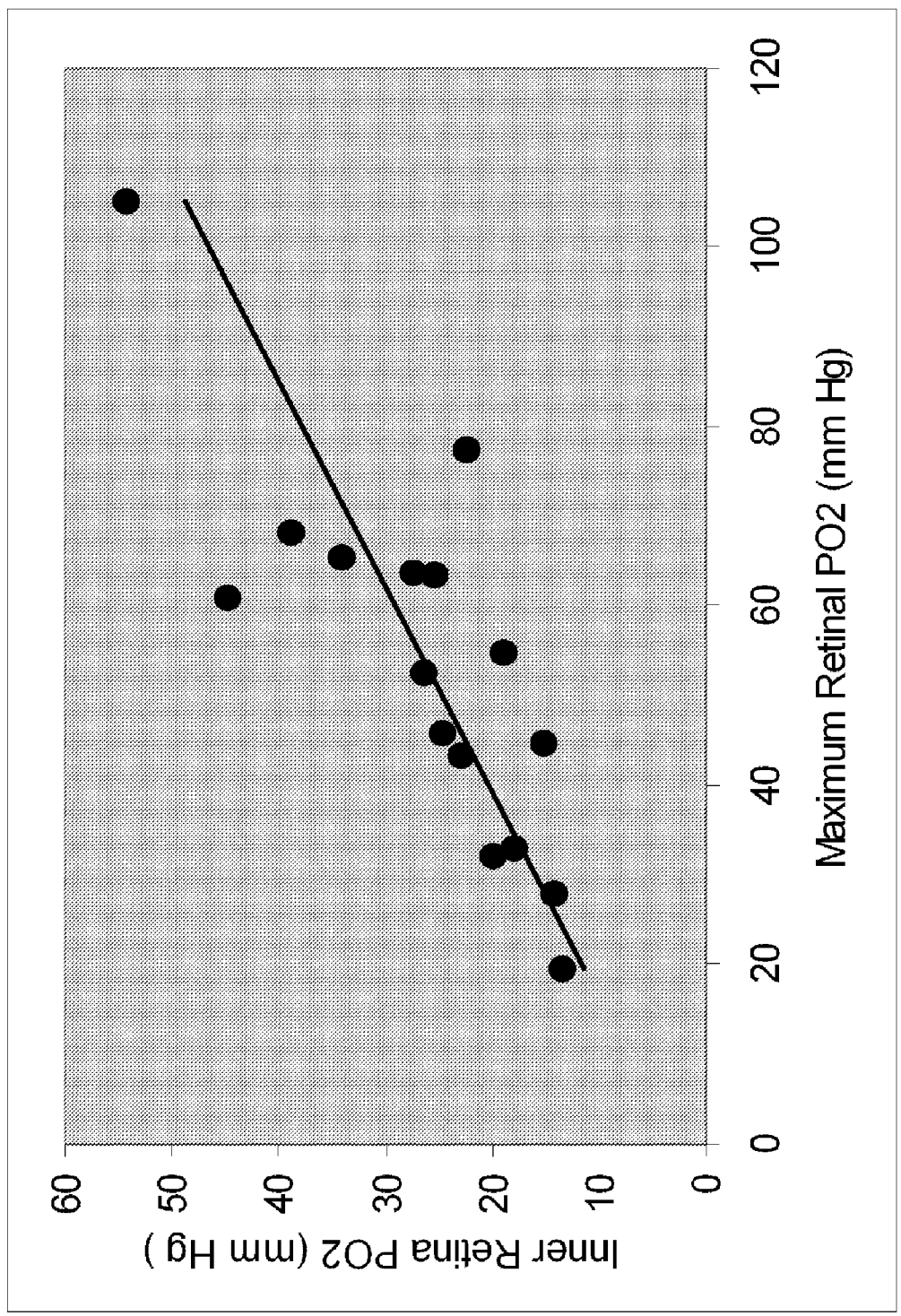
FIG. 7 shows the relationship between mean inner retina $pO_2$ and maximum outer retina $pO_2$.

The relationship between slope of the outer retina $pO_2$ profile and maximum outer retina $pO_2$ is shown in FIG. 6. The slope of the outer retina $pO_2$ profile was negatively correlated with maximum outer retina $pO_2$ (r=0.7; P=0.001). The difference between maximum and minimum outer retina $pO_2$ measurements obtained during $FiO_2$=10%, 21%, and 50% were 13±7, 24±9, and 37±10 mm Hg, respectively, and were significantly different (P=0.003). The relationship between mean inner retina $pO_2$ and maximum outer retina $pO_2$ is shown in FIG. 7. The mean inner retina $pO_2$ was correlated with outer retina $pO_2$ (r=0.8; P<0.001).

Maximum outer retina $pO_2$ increased according to increasing fractions of inspired oxygen. Mean inner retina $pO_2$ was correlated with maximum outer retina $pO_2$.

Retinal $pO_2$ measurements were highly reproducible, providing a reliable means for evaluating the metabolism of retinal tissue. Additionally, measurements of changes in retinal $pO_2$ can be useful for assessment of alterations in retinal oxygen consumption due to retinal diseases.

One skilled in the art will appreciate further features and advantages of the invention based on the above-described embodiments. By way of non-limiting example, the devices and methods of the present invention can employ raster scanning of a point source of illumination light rather than axial scanning of an elongated beam to achieve a 3-dimensional map. Accordingly, the invention is not to be limited by what has been particularly shown and described, except as indicated by the appended claims. All patents, publications and references cited herein are expressly incorporated herein by reference in their entirety.

What is claimed is:

1. A method for determining oxygen tension in a target tissue sensitized with an oxygen sensitive probe comprising:
    obtaining a two-dimensional slice image of a region of the target tissue sensitized with an oxygen sensitive probe;
    scanning to obtain additional two-dimensional slice images through the target tissue, the slice images being offset from each other;
    converting a series of two-dimensional images into a three-dimensional map of oxygen tension within the target tissue; and
    quantifying oxygen tension of the target tissue within the three-dimensional map.

2. The method of claim 1, wherein the step of obtaining a slice image further comprises
    irradiating the target tissue with radiation that induces photoluminescence of the oxygen sensitive probe and
    recording at least one property of the photoluminescence as an image.

3. The method of claim 2 wherein the step of irradiating the target tissue further comprises irradiating the target tissue with an elongated beam of radiation projected at an angle such that a slice image is generated in which tissue photoluminescence is displaced according to depth position.

4. The method of claim 1, wherein the oxygen sensitive probe is a phosphorescent probe.

5. The method of claim 4 wherein the phosphorescent probe emits light of at least one wavelength in a spectrum ranging from about 400 nm to about 900 nm in response to irradiation at an excitation frequency.

6. The method of claim 1, wherein the step of obtaining a two-dimensional slice image further comprises:
    exciting the probe with light to induce secondary light emission;
    detecting the secondary light emission from a two-dimensional region of the target tissue to generate a two-dimensional image of the target tissue, wherein the presence of oxygen quenches the light emitted from the probe.

7. The method of claim 6 wherein the step of quantifying oxygen tension further comprises quantifying a duration of the secondary light emission from a phosphorescent probe.

8. The method of claim 6, wherein the step of quantifying oxygen tension further comprises quantifying an intensity of the secondary light emission from a phosphorescent probe.

9. The method of claim 6, wherein the step of exciting the probe comprises scanning the light at an angle in a vertical line across the tissue to excite the probe in a two-dimensional region of the tissue.

10. The method of claim 1, wherein the target tissue is a chorioretinal tissue.

11. A noninvasive method for monitoring oxygen tension in a chorioretinal tissue region sensitized with an oxygen sensitive probe in a subject comprising:
   obtaining a two-dimensional slice image of a region of the chorioretinal tissue sensitized with an oxygen sensitive probe;
   scanning to obtain additional two-dimensional slice images through the chorioretinal tissue, the slice images being offset from each other;
   converting a series of two-dimensional images into a three-dimensional map of oxygen tension within the chorioretinal tissue; and
   quantifying oxygen tension in the region of the chorioretinal tissue within the three-dimensional map.

12. The method of claim 11 further comprising comparing the quantified oxygen tension of the region with a known standard.

13. An apparatus to determine oxygen tension in tissue, comprises:
   a light source configured to project radiation to excite an oxygen sensitive probe present in a region of tissue and generate a responsive emission;
   a scanner to direct the radiation through a volume of the tissue;
   a detector to capture responsive emissions; and
   a processor for quantifying at least one property of the responsive emissions and generating a three-dimension map of oxygen tension in the volume of the tissue based on variation in the at least one property of the captured responsive emissions.

14. The apparatus of claim 13, wherein the apparatus quantifies at least a duration of responsive emissions.

15. The apparatus of claim 13, wherein the apparatus quantifies at least an intensity of responsive emissions.

16. The apparatus of claim 13, wherein the light source is a diode laser.

17. The apparatus of claim 16, wherein the diode laser generates excitation radiation at a wavelength in the visible spectrum.

18. The apparatus of claim 16, wherein the diode laser generates excitation radiation at a wavelength in a range from about 500 nm to about 600 nm.

19. The apparatus of claim 16, wherein the diode laser generates excitation radiation at a wavelength in a range from about 525 nm to about 550 nm.

20. The apparatus of claim 13, wherein the apparatus further comprises optics for projecting the radiation at an angle relative to a surface of the tissue.

21. The apparatus of claim 13, wherein the apparatus further comprises an optical chopper to periodically interrupt the radiation.

22. The apparatus of claim 13, wherein the apparatus further comprises at least one of a spherical lens and a cylindrical lens to shape the excitation radiation into an elongated beam.

23. The apparatus of claim 13, wherein the scanner has a tracking mechanism to compensate for movement of the tissue.

24. The apparatus of claim 13 further comprises a camera to capture a slice image produced by the responsive emission emitted from the oxygen sensitive probe in response to excitation radiation.

25. The apparatus of claim 24, wherein the camera is a charge-coupled device (CCD).

26. The apparatus of claim 24 further comprises a camera controller to regulate the camera to acquire images at time delayed intervals synchronized with the excitation radiation and thereby acquire a series of slice images offset from each other.

27. The apparatus of claim 24, wherein the processor synchronizes the scanner and the camera to capture the series of slice images.

28. The apparatus of claim 13, wherein the processor is a computer programmed to acquire and store three-dimensional maps of oxygen tension in the volume of tissue.

* * * * *